United States Patent [19]

Hilverda

[11] Patent Number: Plant 7,112

[45] Date of Patent: Jan. 16, 1990

[54] CARNATION NAMED BIANCA

[75] Inventor: Jan J. Hilverda, Aalsmeer, Netherlands

[73] Assignee: Hilverda b.v., Aalsmeer, Netherlands

[21] Appl. No.: 299,757

[22] Filed: Jan. 23, 1989

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation cultivar particularly distinguished by its continuous blooming habit and profuse production of medium sized, substantially pure white flowers borne on erect, rigid stems about 60 cm. in length, the flowers being of medium size with more than three flowers per stem, the plant having a strong, vigorous, upright growth habit with abundant foliage.

1 Drawing Sheet

BACKGROUND OF THE NEW PLANT

This new spray carnation originated as a seedling of a plant resulting from my crossing two unnamed and unpatented carnation varieties selected from my collection of carnation plants maintained by me for breeding purposes at Aalsmeer, The Netherlands, the object of this crossing being to improve the range of varieties for commercial production by having more rapid growth, better flower colors and improved production rate. This particular seedling was selected for propagation because of the almost pure white color of its blooms and propagation was done by me at Aalsmeer by means of cuttings with very satisfactory results. For that reason, this new carnation variety was propagated under my direction for several successive generations by means of cuttings at Aalsmeer, which demonstrated conclusively that this new plant would maintain its distinctive characteristics from generation to generation and that its homgenetic character could be assured for commercial production.

DESCRIPTION OF THE DRAWING

My new spray carnation cultivar is illustrated by the accompanying photographic drawing which shows, in full color, a flower stem having blooms and buds in several stages of maturity, as well as a face view of the flowers, several petals and a bud at the beginning of its opening stage, the colors shown being as nearly true as it is reasonably possible to obtain by conventional photographic procedures.

DESCRIPTION OF THE NEW PLANT

The following is a detailed description of my new spray carnation cultivar based upon observations made during the current year at Aalsmeer, the color designations being according to The R.H.S. Colour Chart published by The Royal Horticultural Society of London, England.

THE PLANT

Origin: Seedling.

Parentage:

*Seed parent.*—An unnamed and unpatented variety.

*Pollen parent.*—An unnamed and unpatented variety. Both varieties having been selected by me from my collection of carnation varieties maintained at Aalsmeer for breeding purposes.

Classification:

*Botanic.*—*Dianthus caryophyllus* L.

*Commercial.*—Spray Carnation.

Form: An erect and tall bush.

Growth: Vigorous, strong and upright.

Branching character: Alternate.

Foliage:

*Quantity.*—Abundant.

*Leaf size.*—Averages about 11 or 12 cm long.

*Shape.*—Elliptic with entire margins.

*Texture.*—Leathery.

*Color.*—Both upper and under side, Blue Green.

*Leaflets.*—None.

*Ribs and veins.*—The midrib is prominent.

THE BUD

Size: Medium.

*Diameter.*—About 15 to 25 mm.

*length.*—About 25 to 30 mm.

Form: Funnel-shaped.

Opening rate: With mature flowers, the flower petals show in approximately five days.

Color of petals: White when sepals first divide and when the petals begin to unfurl.

Sepals:

*Number.*—Five.

*Shape.*—Generally ovate with acute apex.

*Character.*—The sepals are hooded over the bud before dividing and stand up as the flower petals unfurl.

*Color.*—Inside, White to Light Green. Outside, Dark Green.

*Striae.*—Little to minimum in number and of Light Green color.

Calyx:

*Shape.*—Funnel-shaped.

*Size.*—Medium.

*Splitting.*—Very rarely.

*Aspect.*—Smooth.

Flower stem:

*Length.*—Approximately 6 cm.

*Character.*—Rigid and erect.

*Color.*—Dark green.

THE FLOWER

Blooming habit: Continuous with profuse flower production.

Size of bloom: Medium.

*Diameter.*—About 50 to 55 mm.
*Depth.*—About 25 mm.

Borne: In clusters on straight stems emitted in longitudinally-spaced relation from a tall, strong and erect flowering stem.

Flower shape: When bloom first opens, high centered. When bloom matures, it tends to flatten.

Petalage:
*Number of petals.*—Averages about 58 to 60.
*Arrangement.*—Imbricated.
*Form.*—Fan-shaped with dentated margins and acute apex.
*Texture.*—Soft.
*Appearance.*—Velvety.
*Color.*—All petals are white.

Flower stem:
*Length.*—About 60 cm.
*Color.*—Dark green.
*Character.*—Sturdy and upright.

Discoloration after full bloom: None.

Persistence: The flowers hang on and dry.

Fragrance: Medium to strong.

Lasting quality: As a cut flower, ten to fourteen days.

REPRODUCTIVE ORGANS

Stamens:
*Number.*—About 9 to 11.

*Arrangement.*—Evenly arranged around the ovary.
*Anthers.*—Size: Normal. Color: Cream White.
*Filaments.*—Length: About 25 to 30 mm. Color: White.
*Pollen.*—Color: White.

Pistils:
*Number.*—One.
*Style.*—Length: About 25 mm. Color: White.
*Stigma.*—Color: White.

THE FRUIT

Fertility: The fruit is fertile.

Shape: Lozenge-shaped.

Color at maturity: Yellow/Brown.

This carnation cultivar most nearly resembles the variety 'White Lilli-Ann' (unpatented). The new variety is distinguished from 'White Lilli-Ann', however, by more rapid growth, larger flowers and a higher production rate.

I claim:

1. The new and distinct spray carnation variety, substantially as herein shown and described, characterized by its medium sized flowers of substantially pure white color, its profuse production of blooms carried on a long flower stem, and its vigorous and upright growth habit with abundant foliage.

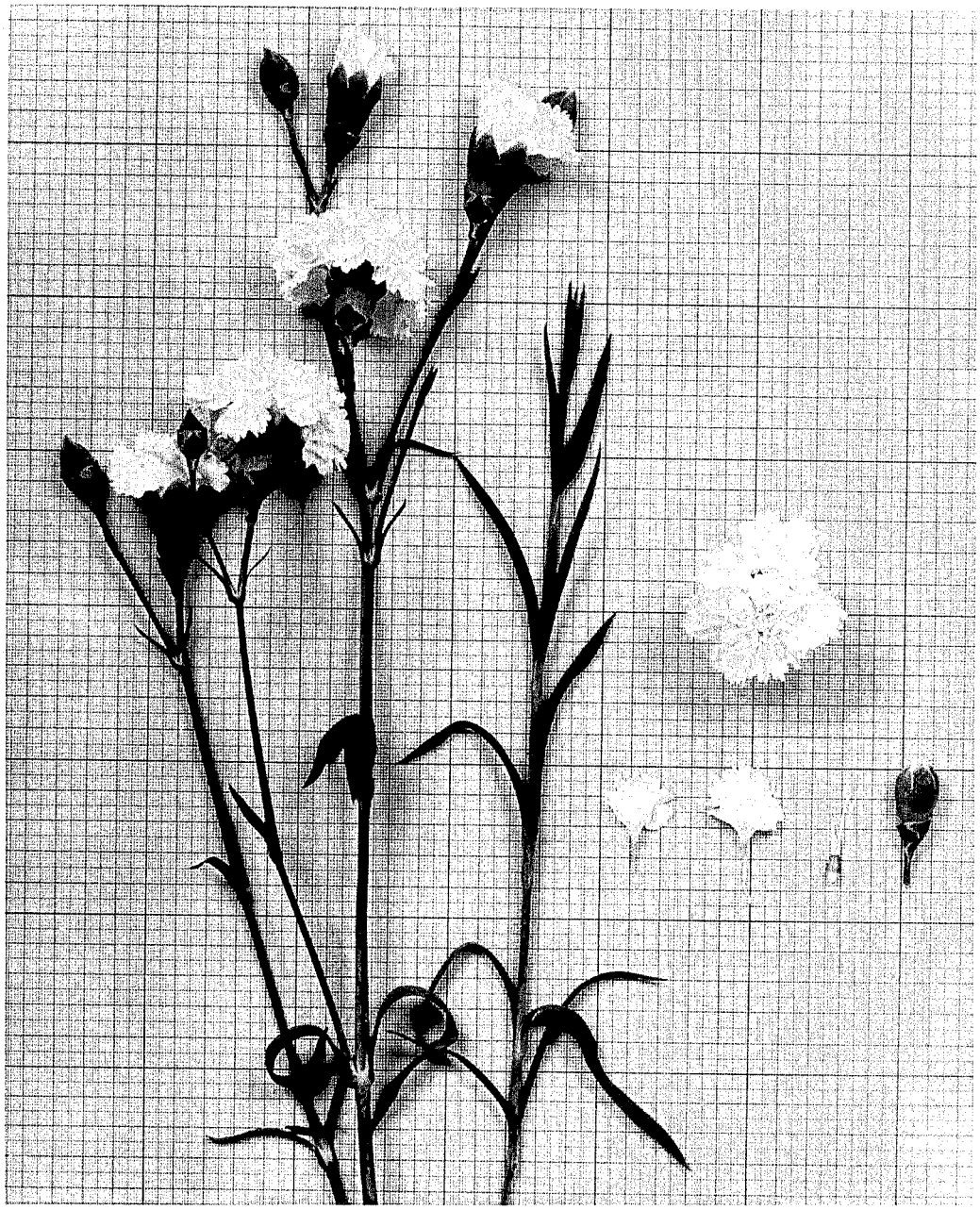

* * * * *